United States Patent [19]

Gormley

[11] 4,376,223

[45] Mar. 8, 1983

[54] METHOD FOR PROMOTING ALUMINUM CHLORIDE CATALYZED ISOMERIZATION OF SYM OCTAHYDROPHENANTHRENE TO SYM-OCTAHYDROANTHRACENE WITH ARYL PHENONE

[75] Inventor: William T. Gormley, Pittsburgh, Pa.

[73] Assignee: Koppers Company, Inc., Pittsburgh, Pa.

[21] Appl. No.: 372,057

[22] Filed: Apr. 26, 1982

[51] Int. Cl.$^3$ ............................ C07C 5/24; C07C 5/30
[52] U.S. Cl. .................................... 585/360; 585/477; 585/478; 585/479
[58] Field of Search ............... 585/360, 477, 478, 479

[56] References Cited

FOREIGN PATENT DOCUMENTS 694961 7/1953 United Kingdom ................ 585/477
2065698 7/1981 United Kingdom ................ 585/477

Primary Examiner—Delbert E. Gantz
Assistant Examiner—A. Pal
Attorney, Agent, or Firm—J. Timothy Keane; Oscar B. Brumback

[57] ABSTRACT

A method is disclosed for promoting isomerization of sym-octahydrophenanthrene (s-OHP) to sym-octahydroanthracene (s-OHA) in the presence of a catalyst provided by aluminum chloride or aluminum bromide, or a mixture of these two compounds. The rate of isomerization is increased by having the reaction run in the presence of an aryl phenone such as benzophenone.

4 Claims, No Drawings

METHOD FOR PROMOTING ALUMINUM CHLORIDE CATALYZED ISOMERIZATION OF SYM OCTAHYDROPHENANTHRENE TO SYM-OCTAHYDROANTHRACENE WITH ARYL PHENONE

BACKGROUND OF THE INVENTION

1. Field of the Invention

Isomerization of sym-octahydrophenanthrene (s-OHP) to sym-octahydroanthracene (s-OHA) in the presence of AlCl₃ catalyst is well known. Of particular interest herein are methods for promoting the rate of isomerization of s-OHP to s-OHA.

2. State of the Art

Anthracene is useful as a starting material in processes for making dyestuffs, antioxidants and medicinals. Anthracene and its isomer phenanthrene are both found in coal tar, with phenanthrene being about four times more abundant than anthracene. Since phenanthrene is more abundant than anthracene, much attention has been given to conversion of phenanthrene to anthracene.

The only practical conversion of phenanthrene to anthracene involves three steps. As a first step, phenanthrene is catalytically hydrogenated to sym-octahydrophenanthrene (s-OHP); secondly, s-OHP undergoes catalyzed isomerization to sym-octahydroanthracene (s-OHA); and thirdly, s-OHA is dehydrogenated to anthracene. In the second step of isomerization of s-OHP to s-OHA, in the presence of AlCl₃ as the isomerization catalyst, known isomerization reactions provide relatively low yields of the desired s-OHA isomer, or relatively high yields of by-product impurities, or typically require relatively long s-OHP-to-catalyst contact times for formation of the s-OHA isomer.

For example, a 1924 German publication [G. Schroeter, *Ber.* 57B, 1990–2003] discloses a reversible isomerization reaction starting with either pure s-OHP or pure s-OHA isomer. In this reversible reaction, 50 percent yields of both s-OHP and s-OHA are obtained from either starting isomer in the presence of small amounts of AlCl₃ at an isomerization temperature in a range of 70° to 80° C. In U.K. Pat. No. 694,961 s-OHP is isomerized to s-OHA in the presence of dispersed, finely-divided AlCl₃ catalyst at an isomerization temperature in a range of 5° to 45° C. Yield of s-OHA ranged from about 70 to 83 weight percent with about 10 to 13 weight percent unidentified by-products. A 1978 West German publication [K. Handrick et al., "Production of Anthracene from Phenanthrene," *Compend.-Dtsch. Ges. Kohlechem.*, 78–79(2), 1089–1106] describes a starting mixture containing s-OHP in the presence of about six weight percent s-OHA. After a 4-hour isomerization period conducted at room temperature, the reaction product mixture contains an equilibrium mixture of s-OHP and s-OHA isomers, there being a maximum of 64 weight percent s-OHA present. U.K. Pat. No. 2,065,698 to Handrick et al. describes isomerization of s-OHP in the presence of 3 to 6 weight percent AlCl₃ catalyst and 15 to 60 weight percent methylene chloride solvent at a temperature of −30° C. to +5° C., which isomerization reaction after a 6- to 7-hour reaction period provides an overall yield of about 94% s-OHA isomer.

There is need, therefore, for s-OHP to s-OHA isomerization processes characterized by an increased yield of s-OHA and an increased rate of isomerization of s-OHP to s-OHA with low yield of by-product impurities.

SUMMARY OF THE INVENTION

In an isomerization process as outlined in Equation I for converting sym-octahydrophenanthrene (s-OHP) to sym-octahydroanthracene (s-OHA) in the presence of a catalyst comprising AlCl₃, or AlBr₃, or a mixture of AlCl₃ and AlBr₃, there is provided an increase in the rate of isomerization by the use of an aryl phenone compound as a promoter in the reaction:

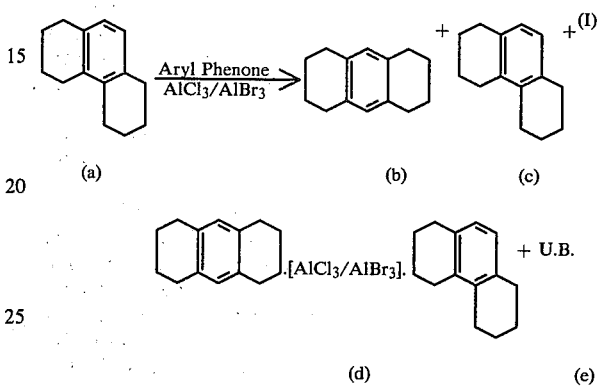

Isomerization of s-OHP starting isomer (a) in the presence of AlCl₃/AlBr₃ catalyst and aryl phenone promoter provides a reaction product mixture containing a major amount of free s-OHA product isomer (b), a minor amount of free unconverted s-OHP starting isomer (c), a three-component isomer-catalyst complex (d) consisting essentially of unconverted s-OHP, s-OHA product and the AlCl₃ or AlBr₃ catalyst, and (e) a small amount of unidentified by-products of an organic nature typically containing residue of the promoter compound. Along with an increase in isomerization rate the process usually provides an increase in yield of the s-OHA isomer.

An increase in the rate of s-OHP to s-OHA isomerization can be accomplished by contacting sym-octahydrophenanthrene with an aryl phenone promoter compound selected from the group of compounds represented by general formula II:

wherein each Ar substituent may be independently selected from a phenyl group, a monomethyl-substituted phenyl group and a dimethyl-substituted phenyl group.

A chief advantage of the process of the invention is that an increase in the rate of conversion of s-OHP to s-OHA allows for optimum isomerization conditions to be established in a relatively shorter period of time. With optimum isomerization conditions established early in the overall isomerization reaction, greater yields of more pure product can be obtained. The process is also advantageous in that a promoter of the defined family of compounds does not destroy or dissolve the aluminum chloride/aluminum bromide catalyst during the isomerization reaction. Also, promoters of the defined family of compounds do not typically react or complex with either of the s-OHA or s-OHP isomers, and thus higher yields of s-OHA product isomer are obtainable.

DETAILED DESCRIPTION OF THE INVENTION

In providing a starting mixture comprising s-OHP starting isomer and AlCl$_3$ or AlBr$_3$ catalyst, or a mixture of the two catalysts, the starting isomer, catalyst and aryl phenone promoter are charged to a reaction vessel equipped with stirring means. An amount of catalyst used is typically about 4 to about 20 weight percent based upon the total weight of the s-OHP isomer in the starting mixture. More typically, about 5 to about 15 weight percent catalyst is used. An amount of promoter used is typically from about 5 to about 50 weight percent based upon the amount of catalyst present in the starting mixture.

Practically any commercially-prepared grade of sym-octahydrophenanthrene may be used as a starting material for conversion to sym-octahydroanthracene in the process of the invention. Typically useful s-OHP starting isomer is prepared by hydrogenation of desulfurized phenanthrene over nickel catalyst by procedures such as shown in U.S. Pat. No. 3,389,188. Commercial grades of aluminum chloride and aluminum bromide are suitable for use as an isomerization catalyst, such as sold by Aldrich Chemical Co., Milwaukee, Wis., and Fisher Scientific Co., Pittsburgh, Pa. Finer particle size materials are preferred over coarser materials.

Aryl phenone compounds of generic formula II which may be used as promoters in the s-OHP to s-OHA isomerization reaction include phenyl-substituted aryl phenones, and include aryl phenones wherein each aryl substituent is provided by a monomethyl-substituted phenyl group, or by a dimethyl-substituted phenyl group, or by a combination of these two types. An example of a preferred aryl phenone is benzophenone, as shown in formula III:

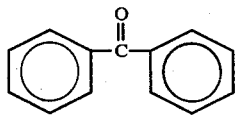

(III)

After determination of the amounts of components to be used in the starting mixture, the selected aryl phenone is mixed with the s-OHP starting isomer to form a solution. Then the powdered AlCl$_3$/AlBr$_3$ catalyst is mixed with the s-OHP-and-promoter solution. The highest conversions of starting isomer are obtained by ensuring even distribution of the catalyst powder and promoter throughout the starting mixture to aid in complexation of the catalyst with the s-OHP isomer. Even distribution is accomplished by thorough mixing of the s-OHP isomer and the catalyst in a mechanical mixer. Practically any conventional mechanical mixer, such as a ball mill or a double-arm mixer, may be used as a reactor for the isomerization reaction; a preferred mixer is an Atlantic helical-action mixer.

Isomerization of s-OHP to s-OHA takes place at room temperature and begins upon addition of the catalyst to the s-OHP isomer. It is known that isomerization of s-OHP isomer to s-OHA isomer typically takes place in two stages, namely, a "mixing" stage and a "standing" stage. During the mixing stage, the s-OHP starting isomer, catalyst and promoter are maintained in intimate contact for a period of time and at a temperature sufficient to convert at least about 70 weight percent of the s-OHP starting isomer to s-OHA product isomer. At about this 70 weight percent conversion point in the isomerization reaction, the viscosity of the reaction mixture increases to an extent so that mixing of the reaction mixture is difficult. In the absence of a promoter, isomerization of s-OHP isomer to 70 percent conversion to s-OHA isomer takes approximately two hours. In the presence of a promoter of the defined family of aryl phenone compounds, isomerization to the 70 percent conversion point takes substantially less than two hours. Generally, mixing occurs with no heat being added except for the waste heat contributed by the mechanical mixer and by the movement of the reaction mass within the reactor. The temperature of the reaction mass is thus typically maintained at about 25° C. during the mixing and standing stages, although reaction temperatures as high as 40° C. and as low as 20° C. may be used with practicality.

Near the end of the mixing stage, a semi-solid mass is formed. This semi-solid reaction mass, typically reddish-brown or dark brown in color, contains free, unconverted s-OHP starting isomer and free s-OHA product isomer. The reaction mass is usually thickened sufficiently after about one hour of mixing so that the dispersed catalyst remains suspended in the reaction mass. Upon achievement of a thickened state of the reaction mass, mixing is usually discontinued inasmuch as conventional mechanical mixers have insufficient mixing capacity to continue movement of the reaction mass. Thereafter, a second stage, the standing stage, of the isomerization process begins.

In the standing stage, the reaction mass is allowed to stand for several hours after the thickened state is achieved. Occasional mixing of the reaction mass may occur during the standing stage, although mixing is not generally required for reaction to proceed. Typically, the reaction mass is maintained in the thickened state for a period of time from about two hours to about four hours, although periods as long as 48 hours may be utilized. During the standing stage, isomerization of s-OHP isomer to s-OHA isomer continues to produce a significant amount of s-OHA product isomer.

At the end of the reaction period, the semi-solid mass provides a reaction-product mixture containing a major amount of free s-OHA product isomer, a minor amount of free, unconverted s-OHP isomer, residue of the promoter compound, and a three-component complex consisting of unconverted s-OHP starting isomer, s-OHA product isomer and the used catalyst. Separation of the free s-OHA and s-OHP isomers from the semi-solid mass is accomplished by contacting the semi-solid mass with separation media provided by a suitable liquid hydrocarbon solvent, or by water, or both.

When a liquid hydrocarbon is used as a separation medium, the hydrocarbon is added in an amount in a volume-ratio-range from about one-to-one to about four-to-one of liquid hydrocarbon solvent to the semi-solid mass, with the hydrocarbon solvent typically at a temperature of about 25° C. After addition and mixing of the liquid hydrocarbon solvent into the semi-solid mass, a liquid phase is formed in contact with undissolved material. The free s-OHP and s-OHA isomers are dissolved into the liquid phase and thereby separated from the insoluble material; this insoluble material contains the isomer-catalyst complex and a small amount of unidentified by-product typically containing residue of the promoter compound.

A liquid hydrocarbon solvent useful for adding to the semi-solid reaction mass to form a liquid phase in contact with undissolved material may be selected from easily-recoverable, non-reactive aliphatic or cycloaliphatic hydrocarbons. The phrase "easily-recoverable, non-reactive" is intended to characterize hydrocarbons which may be easily removed from the dissolved isomers, such as by evaporation, and further which do not form complexes with the catalyst, or with the dissolved isomers, or with other constituents of the reaction-product mixture and moreover which do not dissolve the catalyst. Liquid hydrocarbons satisfying these criteria are typically those which are liquid at about 25° C. and have a boiling point in a range from about 30° C. to about 160° C.; preferably, useful hydrocarbons will have a boiling point from about 30° C. to about 100° C. Examples of suitable aliphatic hydrocarbons are n-pentane, n-hexane, n-decane, n-undecane, 2,2,4-trimethylpentane and petroleum ether mixtures. Examples of suitable cycloaliphatic hydrocarbons are cyclohexane, methylcyclohexane and 1,4-dimethylcyclohexane. A preferred liquid hydrocarbon is n-hexane.

The hydrocarbon-solvent liquid phase containing free unconverted s-OHP starting isomer and free s-OHA product isomer is separated from the undissolved material by decanting or by centrifugal separation. The remaining material may then be washed with subsequent portions of the hydrocarbon solvent, which portions are separated from the undissolved material and combined with the original hydrocarbon-solvent liquid phase. The s-OHP and s-OHA isomers are isolated from the liquid phase by evaporation of the hydrocarbon solvent under reduced pressure, or under a gas stream, with or without the addition of heat. If heat is used to aid in evaporation of the liquid solvent, the temperature of the evaporating liquid should not exceed about 150° C. After removal of the liquid hydrocarbon, there typically remains an off-white liquid which upon cooling to room temperature converts to opaque-white flaky crystals. Separation of the s-OHA and s-OHP isomers from each other is accomplished, if necessary, by fractional crystallization utilizing known techniques.

When water is used as the separation medium, an amount of water is added to the semi-solid mass in a volume ratio of about one-to-one. The water is usually at a temperature in a range from about 70° C. to about 90° C. Addition of water to the semi-solid mass typically causes an exothermic reaction resulting from hydrolysis of the s-OHA.AlCl$_3$/AlBr$_3$.s-OHP complex and subsequent hydration of the AlCl$_3$/AlBr$_3$ catalyst. The presence of heat in the reaction mixture is typically adequate to maintain the s-OHA product isomer as a liquid. Thus there is formed an oily organic phase floating above a water phase. The organic phase is typically composed of s-OHA product isomer, unconverted s-OHP starting isomer, residue of the aryl phenone promoter and unidentified organic by-product. The water phase contains the AlCl$_3$/AlBr$_3$ catalyst.

The organic and water phases are then separated and the organic phase is allowed to cool to room temperature to form a crystalline mass. This mass, which contains predominantly s-OHA product isomer and relatively small amounts of s-OHP starting isomer and other organic materials, may be subjected to conventional dehydrogenation techniques to provide anthracene from its s-OHA precursor. Or, the s-OHA isomer may be separated from the crystalline organic mass by conventional fractional crystallization techniques.

Both water and hexane may be used in combination as a separation medium so that a two-phase system is formed, with an upper layer of hexane containing the s-OHA and s-OHP isomers and other organic materials and with a lower water layer containing the AlCl$_3$/AlBr$_3$ catalyst residue. Isolation of the s-OHA isomer would follow using the described techniques.

The following examples set forth specific embodiments of the invention. The invention is not to be construed, however, as being limited to these embodiments for there are, of course, numerous possible variations and modifications. All parts and percentages of the examples as well as throughout the specification are by weight unless otherwise indicated.

EXAMPLE I

To a glass reaction vessel equipped with magnetic-type stirring means, there were charged 1.0 g reagent grade anhydrous AlCl$_3$ and 10.0 g of water-white liquid sym-octahydrophenanthrene (s-OHP) containing 0.2 g benzophenone. The s-OHP isomer was prepared by hydrogenation of desulfurized phenanthrene over nickel catalyst. These components were maintained in a magnetically-stirred, closed reaction vessel for 1.5 hours at 25° C. Initially, the reaction vessel had a head space of about one-half the total volume of the reaction vessel. No exothermic condition was noted, but the viscosity of the reaction mass increased to an extent sufficient to slow the magnetic stirrer during the latter part of the 1.5-hour reaction period. A reddish-brown semi-solid mass was observed having a volume approximately equal to the original starting materials. Then about 20 ml of hexane was added to the semi-solid mass with mechanical stirring of the mass. The addition of hexane provided a clear solution in contact with a small amount of brown residue at the bottom of the reaction vessel. The clear solution was decanted into a collection vessel. Then, two more additions of 20 ml hexane each were added serially to the residue in the reaction vessel with stirring, and then the resulting solutions were decanted into the collection vessel to give a total hexane solution of approximately 60 ml. The contents of the collection vessel were reduced in volume by evaporation of hexane under a stream of nitrogen at room temperature and under ambient atmospheric pressure. At the end of the evaporation period, residual hexane was removed by heating the contents of the collection vessel to a temperature of about 80° C. for about ten minutes. A concentrated extract was observed in the collection vessel as an off-white liquid at about 80° C. Upon cooling of the off-white liquid to room temperature, opaque-white, flaky crystals formed in an amount of 9.1 g NMR analysis of the crystals formed from the concentrated extract showed a product containing 68 percent by weight of sym-octahydroanthracene and 31 weight percent sym-octahydrophenanthrene and one percent unidentified material. A control experiment which was run in the same manner as above but in the absence of benzophenone promoter resulted in a product weighing 9.2 g and containing 60 percent by weight of sym-octahydroanthracene, 39 weight percent sym-octahydrophenanthrene and one percent unidentified material.

EXAMPLE II

With equipment and under conditions generally as described in Example I, an isomerization reaction was run beginning with 10.0 g of s-OHP, 1.0 g AlCl$_3$ and 0.2 g benzophenone. The reaction period for both the benzophenone promoted mixture and the unpromoted control mixture was 1.5 hours. Organic material in the amount of 9.2 g was recovered from the promoted reaction mixture, which by NMR analysis showed a composition of 70 weight percent s-OHA, 29 weight percent s-OHP and one percent unidentified material. An organic material in the amount of 9.2 g was recovered from the unpromoted control mixture, which by NMR analysis showed a composition of 54 weight percent s-OHA, 45 weight percent s-OHP and one percent unidentified material.

EXAMPLE III

With equipment and under conditions generally as described in Example I, an isomerization reaction was run beginning with 10.0 g of s-OHP, 1.0 g AlCl₃ and 0.4 g benzophenone. The reaction period for both the benzophenone promoted mixture and the unpromoted control mixture was 1.5 hours. Organic material in the amount of 9.4 g was recovered from the promoted reaction mixture, which by NMR analysis showed a composition of 63 weight percent s-OHA, 36 weight percent s-OHP and one percent unidentified material. An organic material in the amount of 9.2 g was recovered from the unpromoted control mixture, which by NMR analysis showed a composition of 54 weight percent s-OHA, 45 weight percent s-OHP and one percent unidentified material.

EXAMPLE IV

With equipment and under conditions generally as described in Example I, an isomerization reaction was run beginning with 10.0 g of s-OHP, 1.0 g AlCl₃ and 0.2 g benzophenone. The reaction period for the benzophenone promoted mixture was carried out for a total of five hours, in order to show the high yields obtainable by the process. No control was run for a similar time. Organic material in the amount of 9.0 g was recovered from the promoted reaction mixture, which by NMR analysis showed a composition of 90 weight percent s-OHA, 9 weight percent s-OHP and one percent unidentified material.

EXAMPLE V

To a 250-ml resin kettle equipped with a mechanical stirrer and means for establishing a nitrogen blanket over a reaction mixture within the kettle, there were charged 100 g water-white liquid sym-octahydrophenanthrene (s-OHP) and 2.0 g benzophenone. This s-OHP was prepared by hydrogenation of desulfurized phenanthrene over nickel catalyst. To this mixture there was added 10.0 g of reagent grade powdered anhydrous AlCl₃. The reaction mixture was stirred for two hours at room temperature. After this reaction period, the reaction mixture was observed to be viscous and reddish-brown in color. About 100 ml of water at a temperature of about 70° C. was added to the viscous reaction mixture with stirring. An exothermic reaction boosted the temperature of the reaction mixture to about 80° C. This mixture was stirred for about three minutes and then allowed to cool to room temperature undisturbed for about one hour. At the end of the cooling period, a solid, off-white organic solid material appeared within the reaction vessel in contact with a clear water solution. The water solution was removed from the vessel leaving behind about 93 g of organic product. NMR analysis of the organic material showed 64 weight percent sym-octahydroanthracene, 31 weight percent sym-octahydrophenanthrene and five percent unidentified material. A control experiment was run in the same manner as above but in the absence of benzophenone promoter. After a two-hour reaction period, there resulted a non-viscous reaction mixture which when treated in accordance with the aforementioned separation steps yielded a reaction product weighing about 80 g and containing 44 weight percent sym-octahydroanthracene, 55 weight percent sym-octahydrophenanthrene and one percent unidentified material.

Although specific examples of the instant invention have been set forth hereinabove, it is not intended that the invention be limited solely thereto, but is to include all the variations and modifications falling within the scope of the appended claims.

What is claimed is:

1. In a process for the isomerization of sym-octahydrophenanthrene to sym-octahydroanthracene in the presence of a catalyst comprising AlCl₃ or AlBr₃, or a mixture thereof, the improvement which comprises using an effective amount of an aryl phenone as a promoter to the catalyst to increase the rate of isomerization as compared with the rate of the unpromoted catalyst whereby the isomerization may be carried out at room temperature.

2. The process of claim 1 wherein the aryl phenone is selected from a group of compounds represented by the general formula

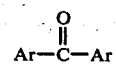

wherein each Ar may be independently selected from a phenyl group, a monomethyl-substituted phenyl group and a dimmethyl-substituted phenyl group.

3. The process of claim 1 wherein said promoter has the structural formula

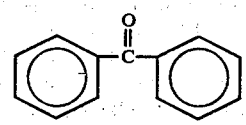

4. The process of claim 1 wherein said catalyst is present in an amount in a range from about 5 to about 15 percent by weight based upon the sym-octahydrophenanthrene initially present and wherein said promoter is present in an amount in a range from about 5 weight percent to about 50 weight percent based upon the amount of catalyst present.

* * * * *